United States Patent
Lund et al.

(10) Patent No.: US 9,631,293 B2
(45) Date of Patent: *Apr. 25, 2017

(54) ELECTRODEPOSITION BATHS, SYSTEMS AND METHODS

(75) Inventors: Alan C. Lund, Framingham, MA (US); Nazila Dadvand, The Woodlands, TX (US); John Cahalen, Arlington, MA (US); Daniel J. Montville, Allston, MA (US)

(73) Assignee: Xtalic Corporation, Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/283,870

(22) Filed: Oct. 28, 2011

(65) Prior Publication Data

US 2012/0043213 A1    Feb. 23, 2012

Related U.S. Application Data

(60) Continuation of application No. 13/117,866, filed on May 27, 2011, now Pat. No. 8,071,387, which is a division of application No. 12/267,010, filed on Nov. 7, 2008, now Pat. No. 7,951,600.

(51) Int. Cl.
| | |
|---|---|
| *C25D 21/00* | (2006.01) |
| *C25D 3/54* | (2006.01) |
| *C25D 3/56* | (2006.01) |
| *C25D 21/12* | (2006.01) |
| *G01N 31/22* | (2006.01) |

(52) U.S. Cl.
CPC .............. *C25D 3/56* (2013.01); *C25D 21/12* (2013.01); *C25D 3/562* (2013.01); *G01N 31/22* (2013.01); *Y10T 436/203332* (2015.01); *Y10T 436/216* (2015.01)

(58) Field of Classification Search
CPC ........................................................ G01N 31/22
USPC ............................... 436/80, 73, 84, 142, 131
See application file for complete search history.

(56) References Cited

U.S. PATENT DOCUMENTS

| | | | |
|---|---|---|---|
| 3,839,465 A * | 10/1974 | Schneider | C07C 41/03 205/271 |
| 4,002,543 A | 1/1977 | Clauss et al. | |
| 4,049,509 A * | 9/1977 | Such | C25D 3/16 205/273 |
| 4,058,439 A | 11/1977 | Tamura et al. | |
| 4,371,397 A * | 2/1983 | Honma | C23C 18/40 106/1.23 |
| 4,525,248 A | 6/1985 | Landa et al. | |
| 5,061,351 A | 10/1991 | Commander et al. | |
| 5,336,380 A | 8/1994 | Phan et al. | |
| 5,352,266 A | 10/1994 | Erb et al. | |
| 5,389,226 A | 2/1995 | Scruggs et al. | |
| 5,525,206 A | 6/1996 | Wieczerniak et al. | |
| 5,853,556 A | 12/1998 | Wieczerniak | |

(Continued)

OTHER PUBLICATIONS

International Search Report from PCT/US09/05967, mailed Mar. 3, 2010.

*Primary Examiner* — Krishnan S Menon
*Assistant Examiner* — Dwan A Gerido
(74) *Attorney, Agent, or Firm* — Wolf, Greenfield & Sacks, P.C.

(57) ABSTRACT

Electrodeposition baths, systems and methods are provided. In some embodiments, the baths, systems and methods are used to deposit metal alloy coatings.

14 Claims, 3 Drawing Sheets

(56) References Cited

U.S. PATENT DOCUMENTS

| | | |
|---|---|---|
| 5,935,405 A | 8/1999 | Wolf et al. |
| 6,036,833 A | 3/2000 | Tang et al. |
| 6,045,682 A | 4/2000 | Rodriguez |
| 6,146,702 A | 11/2000 | Zitko |
| 6,372,118 B1 | 4/2002 | Hui |
| 6,645,364 B2 | 11/2003 | Calvert et al. |
| 6,683,446 B1 | 1/2004 | Pope et al. |
| 6,824,597 B2 | 11/2004 | Heber et al. |
| 6,858,122 B2 | 2/2005 | Kondo et al. |
| 6,890,758 B2 | 5/2005 | Shalyt et al. |
| 7,361,262 B2 | 4/2008 | Dahms et al. |
| 7,425,255 B2 | 9/2008 | Detor et al. |
| 7,442,286 B2 | 10/2008 | Capper et al. |
| 7,521,128 B2 | 4/2009 | Schuh et al. |
| 7,951,600 B2 * | 5/2011 | Lund et al. ............ 436/80 |
| 8,071,387 B1 * | 12/2011 | Lund et al. ............ 436/80 |
| 2002/0060157 A1 | 5/2002 | Calvert et al. |
| 2003/0049850 A1 | 3/2003 | Golden |
| 2004/0000484 A1 * | 1/2004 | Sun ............ G01N 31/164 205/81 |
| 2004/0016644 A1 * | 1/2004 | Isayama et al. ............ 205/82 |
| 2005/0173255 A1 | 8/2005 | Bokisa et al. |
| 2005/0189231 A1 * | 9/2005 | Capper et al. ............ 205/246 |
| 2006/0201820 A1 | 9/2006 | Opaskar et al. |
| 2006/0272949 A1 * | 12/2006 | Detor ............ C25D 3/56 205/238 |
| 2008/0302668 A1 | 12/2008 | Konigshofen et al. |
| 2010/0116675 A1 | 5/2010 | Sklar et al. |
| 2010/0120159 A1 | 5/2010 | Lund et al. |
| 2010/0255596 A1 | 10/2010 | Dadvand et al. |
| 2013/0153430 A1 | 6/2013 | Lund et al. |

\* cited by examiner

ELECTRODEPOSITION BATHS, SYSTEMS AND METHODS

RELATED APPLICATIONS

This application is a continuation of U.S. application Ser. No. 13/117,866 (now U.S. Pat. No. 8,071,387), filed May 27, 2011, which is a divisional of U.S. application Ser. No. 12/267,010 (now U.S. Pat. No. 7,951,600), filed Nov. 7, 2008, which are incorporated herein by reference in their entireties.

FIELD OF INVENTION

This invention relates generally to electrodeposition baths, systems and methods. In some embodiments, the baths, systems and methods are used to deposit metal alloy coatings.

BACKGROUND OF INVENTION

Electrodeposition is a common technique for depositing material on a substrate. Electrodeposition generally involves applying a voltage to a substrate placed in an electrodeposition bath to reduce metal ionic species within the bath which deposit on the substrate in the form of a metal, or metal alloy, coating. The voltage may be applied between an anode and a cathode using a power supply. At least one of the anode or cathode may serve as the substrate to be coated. In some electrodeposition processes, the voltage may be applied as a complex waveform such as in pulse plating, alternating current plating, or reverse-pulse plating.

A variety of metal and metal alloy coatings may be deposited using electrodeposition. For example, metal alloy coatings can be based on two or more transition metals. Tungsten-based coatings are one example of an electrodeposited coating. Such coatings may be tungsten alloys including one or more of the elements Ni, Fe, Co, B, S and P. These coatings often exhibit desirable properties, including high hardness, abrasion resistance, good luster, wear properties, coefficient of friction in sliding applications, amongst others.

Generally, the electrodeposition baths include one or more metal sources as well as additives that may improve the deposition process and/or the resulting coating. The metal source(s) may be selected based on the desired composition of the metallic coating on the article. Typical additives include wetting agent(s), brightening agent(s), leveling agent(s), carrier(s), ductility agent(s), and others.

There is ongoing need for developments of new additives and/or new additive combinations to further improve the deposition process and/or the resulting coating. In particular, there is a need for new additives and/or new additive blends that are effective in electrodeposition processes that use complex waveforms such as in pulse plating, alternating current plating, or reverse-pulse plating.

SUMMARY OF INVENTION

Electrodeposition baths and methods are described.

In one aspect, an electrodeposition bath is provided. The electrodeposition bath comprises tungsten and/or molybdenum ionic species and ionic species of a second metal. The electrodeposition bath further comprises a brightening agent comprising an alkynyl alkoxy alkane compound.

In another aspect, an electrodeposition bath is provided. The electrodeposition bath comprises tungsten and/or molybdenum ionic species and ionic species of a second metal. The electrodeposition bath further comprises a wetting agent comprising a sulfopropylated polyalkoxy napthol compound.

In another aspect, an electrodeposition bath is provided. The electrodeposition bath comprises tungsten and/or molybdenum ionic species and ionic species of a second metal. The electrodeposition bath further comprises a wetting agent comprising an anionic, non-ionic, or amphoteric fluorocarbon compound.

In another aspect, a method for electrodepositing a tungsten- and/or molybdenum-based coating is provided. The method comprises providing an anode, a cathode, an electrodeposition bath associated with the anode and the cathode, and a power supply connected to the anode and the cathode, the electrodeposition bath comprising tungsten and/or molybdenum ionic species, ionic species of a second metal and a brightening agent comprising an alkynyl alkoxy alkane compound. The method further comprises driving the power supply to generate a waveform to electrodeposit a coating on a substrate.

In another aspect, a method for electrodepositing a tungsten- and/or molybdenum-based coating is provided. The method comprises providing an anode, a cathode, an electrodeposition bath associated with the anode and the cathode, and a power supply connected to the anode and the cathode, the electrodeposition bath comprising tungsten and/or molybdenum ionic species, ionic species of a second metal and a wetting agent comprising a sulfopropylated polyalkoxy napthol. The method further comprises driving the power supply to generate a waveform to electrodeposit a coating on a substrate.

In another aspect, a method for electrodepositing a tungsten- and/or molybdenum-based coating is provided. The method comprises providing an anode, a cathode, an electrodeposition bath associated with the anode and the cathode, and a power supply connected to the anode and the cathode, the electrodeposition bath comprising tungsten and/or molybdenum ionic species, ionic species of a second metal and a wetting agent comprising an anionic, non-ionic, or amphoteric fluorocarbon compound. The method further comprises driving the power supply to generate a waveform to electrodeposit a coating on a substrate.

In another aspect, a method for electrodepositing a tungsten- and/or molybdenum-based coating is provided. The method comprises providing an anode, a cathode, an electrodeposition bath associated with the anode and the cathode, and a power supply connected to the anode and the cathode, the electrodeposition bath comprising tungsten and/or molybdenum ionic species, ionic species of a second metal and a brightening agent comprising an alkyne compound. The method further comprises driving the power supply to generate a waveform to electrodeposit a coating on a substrate, the waveform comprising at least one forward pulse and at least one reverse pulse.

In another aspect, a method of analyzing an alkynyl alkoxy alkane compound in an electroplating bath is provided. The method comprises removing a sample from an electroplating bath comprising a tungsten and/or molybdenum ionic species, an ionic species of a second metal, and a brightening agent comprising an alkynyl alkoxy alkane compound and adding a metal compound to the sample to form a metal-bound species by reaction of the alkynyl alkoxy alkane compound with the metal compound. The method further comprises analyzing the metal-bound species.

In another aspect, a method for analyzing an alkyne compound in an electroplating bath is provided. The method comprises removing a sample from an electroplating bath comprising a tungsten and/or molybdenum ionic species, an ionic species of a second metal, a brightening agent comprising an alkynyl alkoxy alkane compound, and a secondary brightening agent comprising an alkyne compound. The method further comprises extracting the alkyne compound from the sample by addition of an organic solvent to the sample, reacting the alkyne with an oxidizing agent to produce a reacted alkyne, and analyzing the reacted alkyne.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

Electrodeposition baths and methods are described. The baths include one or more additives that promote deposition of coatings that exhibit desirable properties and characteristics which can include brightness, surface levelness, reflectivity, hardness and ductility. The coatings, for example, may comprise a tungsten alloy such as a nickel-tungsten alloy. In some cases, the coatings may comprise molybdenum instead of or in addition to tungsten. As described further below, the additives can include a brightening agent comprising an alkynyl alkoxy alkane compound and/or a wetting agent comprising a sulfopropylated polyalkoxy napthol compound. In some embodiments, a brightening agent comprising an alkyne compound is used. The additives have been found to be particularly effective when used in combination with an electrodeposition process that utilizes a complex waveform such as reverse pulse.

Figure 1:
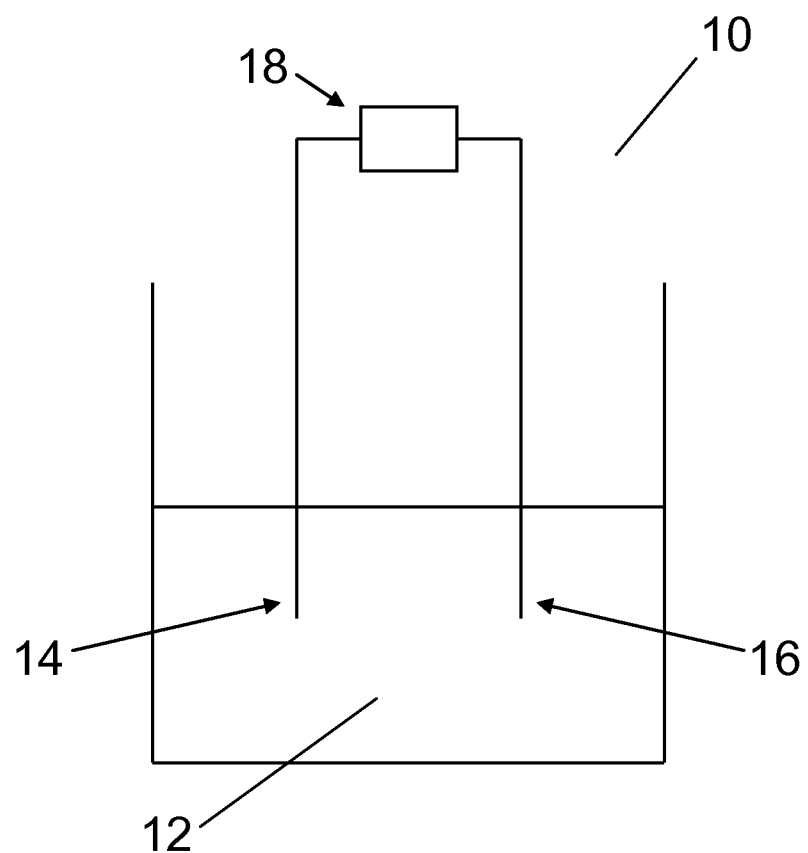
FIG. 1 shows an electrodeposition system according to an embodiment.

FIG. 1 shows an electrodeposition system 10 according to an embodiment. System 10 includes a electrodeposition bath 12. As described further below, the bath includes the metal sources used to form the coating and one or more additives. An anode 14 and cathode 16 are provided in the bath. A power supply 18 is connected to the anode and the cathode. During use, the power supply generates a waveform which creates a voltage difference between the anode and cathode. The voltage difference leads to reduction of metal ionic species in the bath which deposit in the form of a coating on the cathode, in this embodiment, which also functions as the substrate.

It should be understood that the illustrated system is not intended to be limiting and may include a variety of modifications as known to those of skill in the art.

The electrodeposition baths comprise a fluid carrier for the metal source(s) and additive(s). In some embodiments, the fluid carrier is water. However, it should be understood that other fluid carriers may also be used such as molten salts, cryogenic solvents, alcohol baths, amongst others. Those of ordinary skill in the art are able to select suitable fluid carriers.

The pH of the electrodeposition bath can be from about 2.0 to 12.0. In some cases, the electrodeposition bath may have a pH from about 7.0- to 9.0, or, in some cases, from about 7.6 to 8.4, or, in some cases, from about 7.9 to 8.1. However, it should be understood that the pH may be outside the above-noted ranges.

In some cases, the operating range for the electrodeposition baths described herein is 30-100° C., 40-90° C., 50-80° C., or, in some cases, 50-70° C. However, it should be understood that other temperature ranges may also be suitable.

The baths include suitable metal sources for depositing a coating with the desired composition. When depositing a metal alloy, it should be understood that all of the metal constituents in the alloy have sources in the bath. The metal sources are generally ionic species that are dissolved in the fluid carrier. As described further below, during the electrodeposition process, the ionic species are deposited in the form of a metal, or metal alloy, to form the coating. In general, any suitable ionic species can be used. The ionic species may be metal salts. For example, sodium tungstate, ammonium tungstate, tungstic acid, etc. may be used as the tungsten source when depositing a coating comprising tungsten; and, nickel sulfate, nickel hydroxy carbonate, nickel carbonate, nickel hydroxide, etc. may be used as the nickel source to deposit a coating comprising tungsten. In some cases, the ionic species may comprise molybdenum. It should be understood that these ionic species are provided as examples and that many other sources are possible.

As described herein, the electrodeposition baths may include one or more components (e.g., additives) that may enhance the performance of the baths in producing coated articles.

In some embodiments, the baths may include at least one brightening agent. The brightening agent may be any species that, when included in the baths described herein, improves the brightness and/or smoothness of the metal coating produced. In some cases, the brightening agent is a neutral species. In some cases, the brightening agent comprises a charged species (e.g., a positively charged ion, a negatively charged ion). In one set of embodiments, the brightening agent may comprise an alkyl group, optionally substituted. In some embodiments, the brightening agent may comprise a heteroalkyl group, optionally substituted.

In some cases, the brightening agent may be an alkynyl alkoxy alkane. For example, the brightening agent may comprise a compound having the following formula,

wherein n is an integer between 1 and 100, and $R^1$ is alkyl or heteroalkyl, optionally substituted. In some cases, the $R^1$ is an alkyl group, optionally substituted with OH or $SO_3$. In some embodiments, $R^1$ comprises a group having the formula $(R^2)_m$, wherein $R^2$ is alkyl or heteroalkyl, optionally substituted, and m is an integer between 3 and 103, such that n is less than or equal to (m−2). In some embodiments, n is an integer between 1 and 5. In some embodiments, m is an integer between 3 and 7. Some specific examples of brightening agents include, but are not limited to, propargyl-oxopropane-2,3-dihydroxy (POPDH) and propargyl-3-sulfopropyl ether Na salt (POPS). It should be understood that other alkynyl alkoxy alkanes may also be useful as brightening agents.

In some cases, the brightening agent may comprise an alkyne. For example, the alkyne may be a hydroxy alkyne. In some embodiments, the brightening agent may comprise a compound having the following formula,

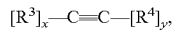

wherein $R^3$ and $R^4$ can be the same or different and each is H, alkyl, hydroxyalkyl, or amino optionally substituted, and x and y can the be same or different and each is an integer between 1 and 100. In some cases, at least one of $R^3$ or $R^4$ comprises a hydroxyalkyl group. In some instances, at least one of $R^3$ or $R^4$ comprises an amino functional group. In some embodiments, x and y can be the same or different and are integers between 1-5, and at least one of $R^3$ and $R^4$ comprises a hydroxyalkyl group. In an illustrative embodiment, the alkyne is 2-butyne-1,4-diol. In another illustrative embodiment, the alkyne is 1-diethylamino-2-propyne. It should be understood that other alkynes may also be useful as brightening agents within the context of the invention.

In some cases, the brightening agent may be chosen from those molecules falling within the betain family, where a betain is a neutrally charged compound comprised of a positively charged cationic functional group and a negatively charged anionic functional group. Here examples of the cationic side of the betain could be ammonium, phosphonium, or pyridinium groups optionally substituted, and examples of the anionic side could be carboxylic, sulfonic, or sulfate groups. It should be understood that these functional groups are for illustration and are not intended to be limiting.

In some cases, the electrodeposition baths may include a combination of at least two brightening agents. For example, a bath may comprise both a brightening agent comprising an alkynyl alkoxy alkane and a second brightening agent comprising an alkyne.

The baths may comprise the brightening agent in a concentration of from 0.05 g/L to 5 g/L, from 0.05 g/L to 3 g/L, from 0.05 g/L to 1 g/L, or, in some cases, from 0.01 g/L to 1 g/L. In some cases, the baths may comprise the brightening agent in a concentration of from 0.05 g/L to 1 g/L, from 0.05 g/L to 0.50 g/L, from 0.05 g/L to 0.25 g/L, or, in some cases, from 0.05 g/L to 0.15 g/L. Those of ordinary skill in the art would be able to select the concentration of brightening agent, or mixture of brightening agents, suitable for use in a particular application.

Those of ordinary skill in the art would be able to select the appropriate brightening agent, or combination of brightening agents, suitable for use in a particular invention. In some embodiments, the alkynyl alkoxy alkane, alkyne, or other brightening agent may be selected to exhibit compatibility (e.g., solubility) with the eletroplating bath and components thereof. For example, the brightening agent may be selected to include one or more hydrophilic species to provide greater hydrophilicity to the brightening agent. The hydrophilic species can be, for example, amines, thiols, alcohols, carboxylic acids and carboxylates, sulfates, phosphates, polyethylene glycols (PEGs), or derivatives of polyethylene glycol. The presence of a hydrophilic species can impart enhanced water solubility to the brightening agent. For example, $R^1$, $R^2$, and/or $R^3$ as described above may be selected to comprise a hydroxyl group or a sulfate group.

In some cases, the baths may include at least one wetting agent. A wetting agent refers to any species capable of increasing the wetting ability of the electrodeposition bath with the surface of the article to be coated. For example, the substrate may comprise a hydrophilic surface, and the wetting agent may enhance the compatibility (e.g., wettability) of the bath relative to the substrate. In some cases, the wetting agent may also reduce the number of defects within the metal coating that is produced. The wetting agent may comprise an organic species, an inorganic species, an organometallic species, or combinations thereof. In some embodiments, the wetting agent may be selected to exhibit compatibility (e.g., solubility) with the eletroplating bath and components thereof. For example, the wetting agent may be selected to include one or more hydrophilic species, including amines, thiols, alcohols, carboxylic acids and carboxylates, sulfates, phosphates, polyethylene glycols (PEGs), or derivatives of polyethylene glycol, to enhance the water solubility of the wetting agent.

In one set of embodiments, the wetting agent may comprise an aromatic group, optionally substituted. For example, the wetting agent may comprise a naphthyl group substituted with one or more an alkyl or heteroalkyl group, optionally substituted.

In some cases, the wetting agent may comprise a sulfopropylated polyalkoxy napthol having the following formula,

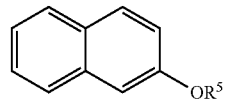

wherein $R^5$ comprises an alkyl or heteroalkyl group. In some cases, $R^5$ comprises a charged group, such as $SO_3$. For example, the wetting agent may comprise the group, $-(CH_2)_3SO_3$. In some embodiments, $R^5$ may comprise a group having the formula $(R^6)_q$, wherein $R^6$ is alkyl or heteroalkyl, optionally substituted, and q is an integer between 1-100. In an illustrative embodiment, the wetting agent may be Ralufon NAPE 14-90 (Raschig GmbH).

In another set of embodiments, the wetting agent may comprise a fluorocarbon, optionally substituted. The fluorocarbon could be fully or partially fluorinated. The wetting agent could be chosen from the groups of anionic, non-ionic and amphoteric fluorocarbons. For example, an anionic wetting agent may comprise a fluorocarbon substituted with an anionic moiety such as a carboxylate, sulfonate, sulfate, phosphate, etc. An example of an anionic fluorinated wetting agent is $C_8F_{17}SO_3Na$. Non-ionic wetting agents are substantially non-dissociated in an electroplating bath, for example $C_8F_{17}-CH_2-CH_2-O-(CH_2-CH_2-O)_n-H$. Amphoteric wetting agents have at least one anionic and cationic moiety. An example of an amphoteric fluorinated wetting agent is $C_6F_{13}-(CH_2)_2-SO_2-HN-(CH_2)_3-N(CH_3)_2-CH_2-COOH$.

Additives described herein can be used both individually and/or in any combinations thereof to provide improved coating quality through brightening, leveling and reduction in propensity for surface pitting.

In some embodiments, the electrodeposition bath may include additional additives. For example, the electrodeposition bath may comprise one or more complexing agents. A complexing agent refers to any species which can coordinate with the metallic ions contained in the solution. The complexing agent may be an organic species, such as a citrate ion, or an inorganic species, such as an ammonium ion. In some cases, the complexing agent is a neutral species. In some cases, the complexing agent is a charged species (e.g., negatively charged ion, positively charged ion). Examples of complexing agents include citrates, gluconates, tartrates, and other alkyl hydroxyl carboxylic acids. Generally, a complexing agent, or mixture of complexing agents, may be included in the electrodeposition bath within a concentration range of 10-200 g/L, and, in some cases, within the range of 40-80 g/L. In one embodiment, the complexing agent is a citrate ion. In some embodiments, ammonium ions may be incorporated into the electrolyte bath as complexing agents and to adjust solution pH. For example, the electrodeposition bath may comprise ammonium ions in the range of 1-50 g/L, and between 10-30 g/L.

Those of ordinary skill in the art would be able to select the appropriate combination of brightening agent, wetting agent, and/or other additives suitable for use in a particular application. For example, a screening test for selection of a bath component may include electroplating a coating using a particular bath composition as described herein, or series of bath compositions, and comparing the resulting coating(s) formed to determine the bath composition that produces the desired coating or coating characteristic. In one set of embodiments, a series of bath compositions, each including a different brightening agent, may be used to electroplate a series of coatings. The characteristics (e.g., appearance, stability, etc.) of the resulting coatings may then be evaluated to select the appropriate brightening agent. Similar screening tests may also be employed for other bath components, including wetting agent and/or other additives.

As used herein, the term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The alkyl groups may be optionally substituted, as described more fully below. Examples of alkyl groups include, but are not limited to, methyl, ethyl, propyl, isopropyl, butyl, isobutyl, tert-butyl, 2-ethylhexyl, cyclopropyl, cyclobutyl, cyclopentyl, cyclohexyl, and the like. "Heteroalkyl" groups are alkyl groups wherein at least one atom is a heteroatom (e.g., oxygen, sulfur, nitrogen, phosphorus, etc.), with the remainder of the atoms being carbon atoms. Examples of heteroalkyl groups include, but are not limited to, alkoxy, poly(ethylene glycol)-, alkyl-substituted amino, tetrahydrofuranyl, piperidinyl, morpholinyl, etc.

The terms "alkenyl" and "alkynyl" refer to unsaturated aliphatic groups analogous to the alkyl groups described above, but containing at least one double or triple bond respectively. The "heteroalkenyl" and "heteroalkynyl" refer to alkenyl and alkynyl groups as described herein in which one or more atoms is a heteroatom (e.g., oxygen, nitrogen, sulfur, and the like).

As used herein, the term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted heteroalkyl" must still comprise the heteroalkyl moiety and can not be modified by substitution, in this definition, to become, e.g., an alkyl group. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, aralkyl, cyclic alkyl, heterocycloalkyl, hydroxy, alkoxy, aryloxy, perhaloalkoxy, aralkoxy, heteroaryl, heteroaryloxy, heteroarylalkyl, heteroaralkoxy, azido, amino, halogen, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, alkoxyalkyl, perhaloalkyl, arylalkyloxyalkyl, and the like.

In some aspects, various techniques can be used to monitor the contents of the electrodeposition baths. For example, the techniques may determine the concentration of one or more of the additives in the bath such as the brightening agent(s), wetting agent(s), complexing agent(s), etc. If the concentration of the additive(s) is below or above a desired concentration, the bath composition may be adjusted so that the concentration lies within the desired range.

In some embodiments, techniques for determining the concentration of a brightening agent comprising an alkyne (e.g. a hydroxy alkyne) compound, are provided. In some cases, the compound may be a diol, such a 2-butyne-1,4-diol. The techniques generally involve removing a sample from the electroplating bath. In some instances, an oxidizing agent is reacted with the alkyne to produce a reacted alkyne. As described below, the reacted alkyne may be analyzed. In some methods, the alkyne is extracted from a sample taken from the electrodeposition bath using a solvent (e.g., an organic solvent, such as butyl acetate). The solvent containing the alkyne, in some cases, is treated with an aqueous solution containing an oxidizing agent (e.g. potassium permanganate, a chromium compound, etc.) to produce a reacted alkyne and a distinguishable color change. In some instances, using colorimetry, the solution having a distinguishable color can be compared to a set of colored solutions generated using a known quantity of alkyne to determine the concentration of alkyne in the electrodeposition bath. By determining the concentration of alkyne in the electrodeposition bath, adjustments can be made to the electrodeposition bath to produce a desired concentration of alkyne.

In other embodiments, the invention provides techniques for determining the concentration of a brightening agent comprising an alkynyl alkoxy alkane compound. In some embodiments, the alkynyl alkoxy alkane compound can be a terminal alkyne, such as POPS and/or POPDH. The techniques generally involve removing a sample from the electroplating bath. In some methods, a metal compound is added to the sample which reacts with the alkynyl alkoxy alkane compound to form a metal-bound species. As described further below, the metal-bound species may be analyzed. In some methods, the pH of the sample is adjusted to a value above pH 7 (e.g., about pH 8) by the addition of an alkaline solution (e.g., aqueous sodium hydroxide) prior to adding the metal compound. In some methods, the alkynyl alkoxy alkane can be precipitated when the metal compound is added to form the metal-bound species, which may be in the form of a suspension of particles in solution. Some examples of suitable metal compounds for precipitation of the alkynyl alkoxy alkane are silver compounds (e.g. silver nitrate) and/or copper compounds [e.g. copper(I) chloride]. The turbidity of the metal-bound species, which may be in the form of a suspension of particles, can be measured using, for example, a turbidity meter. A standard curve for alkynyl alkoxy alkane concentration versus turbidity can be generated, for example, using the turbidity values of a set of solutions containing a range of known concentrations of the alkynyl alkoxy alkane and plotting the turbidity values against the known concentrations of the alkynyl alkoxy alkane. Fitting a curve to the resultant plot, using a method such as a linear regression, can allow the derivation of a general mathematical formula for calculating the concentration of the alkynyl alkoxy alkane in a sample having an unknown concentration of the alkynyl alkoxy alkane by inputting the turbidity value of the sample into the formula.

In other instances, potentiometry can be used to analyze the metal-bound species. In some methods, the amount of unreacted metal compound in the sample is determined by potentiometric titration and is used to calculate the amount of metal-bound species formed by the reaction of the metal compound with the alkynyl alkoxy alkane. In some embodiments, a thiocyanate (e.g. potassium thiocyanate) solution is used to titrate the sample containing the unreacted metal compound and determine the amount of metal compound remaining after reaction of the metal compound with the alkynyl alkoxy alkane. Generally, the amount of metal-bound species formed by reaction of the metal compound with the alkynyl alkoxy alkane is proportional to the amount of the metal compound consumed during the reaction and can be calculated by subtracting the amount of metal compound remaining after reaction of the metal compound with the alkynyl alkoxy alkane from the initial amount of metal compound added to the sample. As described above for analyzing the metal-bound species by measuring turbidity, an analogous standard curve for alkynyl alkoxy alkane concentration versus amount of titrant consumed can be generated, thereby allowing a mathematical formula for calculating the concentration of the alkynyl alkoxy alkane in a sample having an unknown concentration of the alkynyl alkoxy alkane to be derived. By determining the concentration of alkynyl alkoxy alkane in the electrodeposition bath, adjustments can be made to the electrodeposition bath to produce a desired concentration of alkynyl alkoxy alkane.

In additional embodiments, a method is provided for determining the concentration of a wetting agent. In some instances, the wetting agent comprises a sulfopropylated polyalkoxy napthol such as Ralufon NAPE 14-90. An electrodeposition bath sample can be combined with a solvent (e.g. chloroform) and an indicator solution. In one example, the indicator solution comprises two indicator dyes such as dimidium bromide and patent blue. The mixture containing the sample, solvent, and indicator solution can be titrated with a titrating agent until a distinguishable color change can be observed. In some instances, the solvent in the mixture is pink in color, and benzethonium chloride (a titrating agent) is added to the mixture until the solvent is blue in color. A standard curve for wetting agent concentration versus amount of benzethonium chloride titrated can be generated, for example, using the amount of benzethonium chloride titrated in a set of solutions containing a range of known concentrations of the wetting agent and plotting the amount of benzethonium chloride titrated against the known concentrations of the wetting agent. Fitting a curve to the resultant plot, using a method such as a linear regression, can allow the derivation of a general mathematical formula for calculating the concentration of the wetting agent in a sample having an unknown concentration of the wetting agent by inputting the amount of benzethonium chloride titrated in the mixture of sample, solvent, and indicator solution into the formula. By determining the concentration of wetting agent in the electrodeposition bath, adjustments can be made to the electrodeposition bath to produce a desired concentration of wetting agent.

In general, the electrodeposition baths can be used in connection with any electrodeposition process. Electrodeposition generally involves the deposition of a coating on a substrate by contacting the substrate with an electrodeposition bath and flowing electrical current between two electrodes through the electrodeposition bath, i.e., due to a difference in electrical potential between the two electrodes. For example, methods described herein may involve providing an anode, a cathode, an electrodeposition bath associated with (e.g., in contact with) the anode and cathode, and a power supply connected to the anode and cathode. In some cases, the power supply may be driven to generate a waveform for producing a coating, as described more fully below. In some embodiments, at least one electrode may serve as the substrate to be coated.

The electrodeposition may be modulated by varying the potential that is applied between the electrodes (e.g., potential control or voltage control), or by varying the current or current density that is allowed to flow (e.g., current or current density control). In some embodiments, the coating may be formed (e.g., electrodeposited) using direct current (DC) plating, pulsed current plating, reverse pulse current plating, or combinations thereof. Pulses, oscillations, and/or other variations in voltage, potential, current, and/or current density, may also be incorporated during the electrodeposition process, as described more fully below. For example, pulses of controlled voltage may be alternated with pulses of controlled current or current density. In general, during an electrodeposition process an electrical potential may exist on the substrate to be coated, and changes in applied voltage, current, or current density may result in changes to the electrical potential on the substrate. In some cases, the electrodeposition process may include the use of waveforms comprising one or more segments, wherein each segment involves a particular set of electrodeposition conditions (e.g., current density, current duration, electrodeposition bath temperature, etc.), as described more fully below.

In some embodiments, a coating, or portion thereof, may be electrodeposited using direct current (DC) plating. For example, a substrate (e.g., electrode) may be positioned in contact with (e.g., immersed within) a electrodeposition bath comprising one or more species to be deposited on the substrate. A constant, steady electrical current may be passed through the electrodeposition bath to produce a coating, or portion thereof, on the substrate.

In some cases, the electrodeposition method involves driving a power supply to generate a waveform to electrodeposit a coating. The waveform may have any shape, including square waveforms, non-square waveforms of arbitrary shape, and the like. As described further below, in some methods such as when forming coatings having different portions, the waveform may have different segments used to form the different portions. However, it should be understood that not all methods use waveforms having different segments.

In some cases, a bipolar waveform may be used, comprising at least one forward pulse and at least one reverse pulse, i.e., a "reverse pulse sequence." As noted above, the electrodeposition baths described herein are particularly well suited for depositing coatings using complex waveforms such as reverse pulse sequences. In some embodiments, the at least one reverse pulse immediately follows the at least one forward pulse. In some embodiments, the at least one forward pulse immediately follows the at least one reverse pulse. In some cases, the bipolar waveform includes multiple forward pulses and reverse pulses. Some embodiments may include a bipolar waveform comprising multiple forward pulses and reverse pulses, each pulse having a specific current density and duration. In some cases, the use of a reverse pulse sequence may allow for modulation of composition and/or grain size of the coating that is produced.

Figure 2:
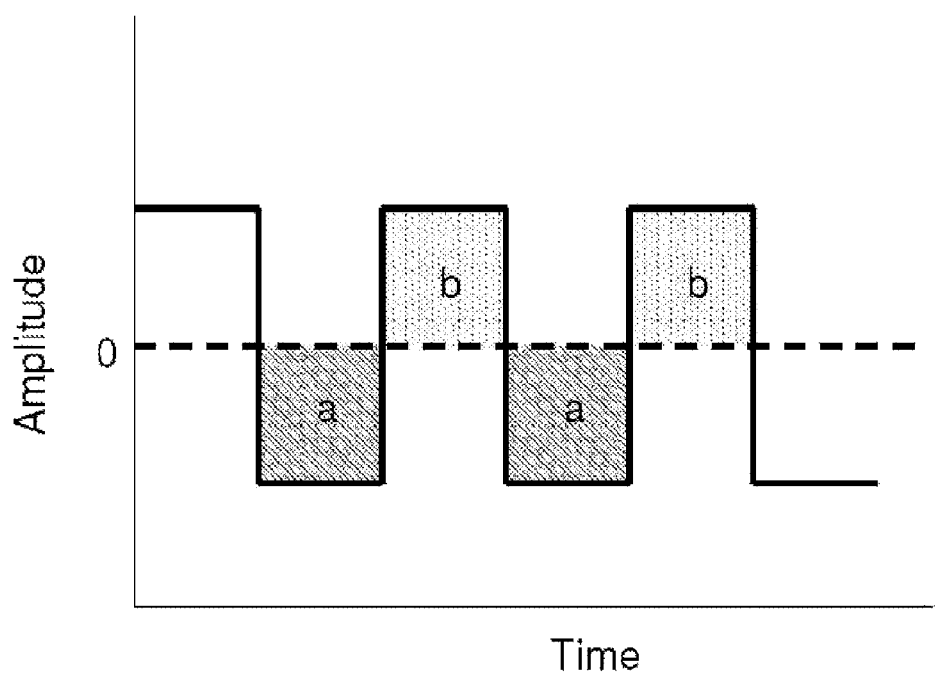
FIG. 2 shows an example of a waveform comprising a reverse pulse sequence according to an embodiment.

In some embodiments, a reverse pulse sequence may be applied such that the forward (e.g., positive) current density, when integrated over the duration of the forward current pulse(s), is of a similar magnitude to the reverse (e.g., negative) current density integrated over the duration of the reverse current segment. FIG. 2 shows an example of a reverse pulse sequence, wherein portions A represent the reverse current density integrated over the duration of the reverse current pulse(s) and portions B represent the forward current density integrated over the duration of the forward current pulse(s).

Figure 3:
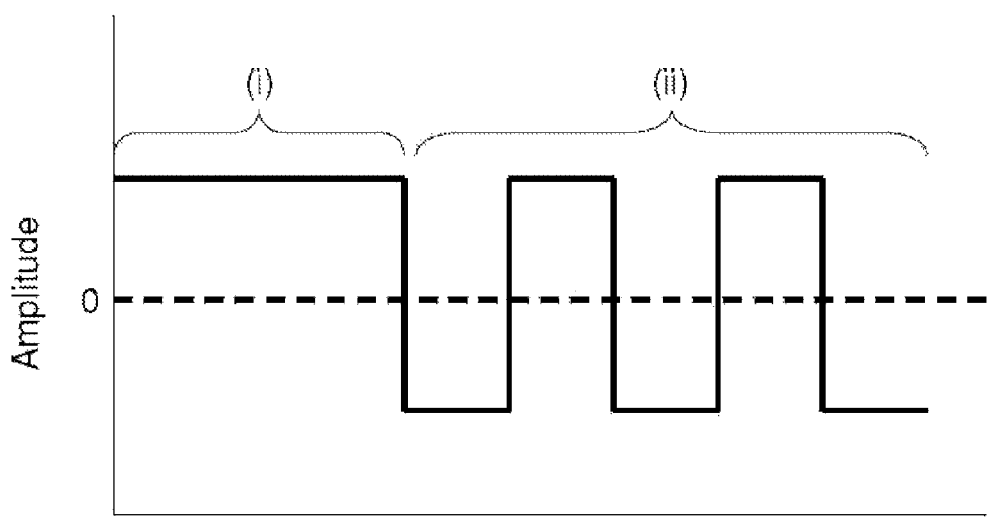
FIG. 3 shows an example of a waveform comprising (i) a first segment including a single, forward pulse and (ii) a second segment including a reverse pulse sequence.

As noted above, some embodiments may include a waveform having more than one segment, each segment including a particular set of electrodeposition conditions. That is, the waveform is different in different segments. For example, the waveform may include one segment comprising at least one forward pulse and at least one reverse pulse (e.g., a bipolar waveform or a reverse pulse sequence), and another segment comprising a single forward, or reverse, pulse. In some cases, the segment having the single pulse may be arranged prior to the segment having the reverse pulse sequence. For example, FIG. 3 shows an example of a waveform comprising (i) a first segment including a single, forward pulse and (ii) a second segment including a reverse pulse sequence, according to one embodiment of the invention. In some cases, the second segment is similar to the waveform shown in FIG. 2. It also should be understood that the waveform may have more segments in addition to the first and second segments.

The methods of the invention may utilize certain aspects of methods described in U.S. Patent Publication No. 2006/02722949, entitled "Method for Producing Alloy Deposits and Controlling the Nanostructure Thereof using Negative Current Pulsing Electro-deposition, and Articles Incorporating Such Deposits," which is incorporated herein by reference in its entirety. Aspects of other electrodeposition methods may also be suitable including those described in U.S. Patent Publication No. 2006/0154084 and U.S. application Ser. No. 11/985,569, entitled "Methods for Tailoring the Surface Topography of a Nanocrystalline or Amorphous Metal or Alloy and Articles Formed by Such Methods", filed Nov. 15, 2007, and U.S. patent application Ser. No. 12/120,564, filed May 14, 2008 which are incorporated herein by reference in their entireties.

The coating comprises one or more metals. For example, the coating may comprise an alloy (e.g., a nickel-tungsten alloy). Examples of suitable alloys may include two or more of the following elements: Ni, W, Fe, B, S, Co, Mo, Cu, Cr, Zn and Sn, amongst others. In some cases, alloys that comprises tungsten (e.g., nickel-tungsten alloys) are particularly preferred. Some specific examples of alloys include Ni—W, Ni—Fe—W, Ni—B—W, Ni—S—W, Co—W, Ni—Mo, Co—Mo and Ni—Co—W.

In some cases, the coating may be combined with additional phases. For example, hard particulates of metal, ceramic, intermetallic, or other material might be incorporated into the coating. Other potential phases which may be incorporated will also be recognized by those skilled in the art, such as solid lubricant particles of graphite or $MoS_2$.

In some embodiments, it may be advantageous for the coating to be substantially free of elements or compounds having a high toxicity or other disadvantages. In some embodiments, it may be advantageous for the coating to be substantially free of elements or compounds that are deposited using species that have a high toxicity or other disadvantages. For example, in some cases, the coating may be free of chromium (e.g., chromium oxide) since it is often deposited using chromium ionic species (e.g., $Cr^{6+}$) which are toxic. Such coatings may provide various processing, health, and environmental advantages over previous coatings.

The coating may have any thickness suitable for a particular application. For example, the total coating thickness may be between 10 nm and 1 mm; in some cases, between 100 nm and 200 micron; and, in some cases, between 100 nm and 100 micron.

It should be understood, however, that the coating may also have other thicknesses outside the above-noted ranges.

In some cases, the coatings may have a particular microstructure. For example, at least a portion of the coating may have a nanocrystalline microstructure. As used herein, a "nanocrystalline" structure refers to a structure in which the number-average size of crystalline grains is less than one micron. The number-average size of the crystalline grains provides equal statistical weight to each grain and is calculated as the sum of all spherical equivalent grain diameters divided by the total number of grains in a representative volume of the body. In some embodiments, at least a portion of the coating may have an amorphous structure. As known in the art, an amorphous structure is a non-crystalline structure characterized by having no long range symmetry in the atomic positions. Examples of amorphous structures include glass, or glass-like structures. Some embodiments may provide coatings having a nanocrystalline structure throughout essentially the entire coating. Some embodiments may provide coatings having an amorphous structure throughout essentially the entire coating.

Various substrates may be coated to form coated articles, as described herein. In some cases, the substrate may comprise an electrically conductive material, such as a metal, metal alloy, intermetallic material, or the like. Suitable substrates include steel, copper, aluminum, brass, bronze, nickel, polymers with conductive surfaces and/or surface treatments, transparent conductive oxides, amongst others.

The following examples are provided for illustration purposes and are not intended to be limiting.

EXAMPLES

Several experiments were conducted to illustrate some embodiments of the present inventions. The experiments involved coatings of Ni—W alloys produced by aqueous electrodeposition.

Example 1

This example demonstrates the use of alkynyl alkoxy alkanes, as brightening agents in the deposition of Ni—W alloy coatings. Brushed steel articles were coated with Ni—W alloys by electrodeposition from an aqueous electrodeposition bath. Each article was immersed in an electrodeposition bath, and a DC current was applied using stainless steel counter electrodes. A 267 mL Hull Cell operating at 3 amperes and 60° C. for 10 minutes with air agitation of the electrodeposition bath was used to produce the coated articles. Coated articles formed using this method provided a current density evaluation range of about 0 amperes per square foot (ASF) to 225 ASF. Articles were chemically prepared prior to plating as is well known in the art.

TABLE 1

| Solution A composition. | |
| --- | --- |
| Nickel metal (from nickel sulfate) | 6.5 g/L |
| Tungsten metal (from sodium tungstate) | 32.5 g/L |
| Citric acid | 64 g/L |
| Ammonium hydroxide to pH ~8.0 | ~20 g/L |
| Sufficient water to produce 1 L of solution | |

Solution A was used as the basic electrolyte solution for the electrodeposition baths demonstrated in this example, and brightening agents from the family of alkynyl alkoxy alkanes were added to this solution in concentrations from 0 to ~0.5 g/L. A hull cell test panel was prepared as described above from Solution A with no additives, and the resulting Ni—W alloy coating produced from this solution was matte/semi-bright below a current density of 20 ASF and hazy/matte greater than a current density of 20 ASF. Article 1A served as the reference sample for comparison to articles coated using electrodeposition baths containing additives.

Articles 1B-F were produced from electrodeposition baths containing Solution A and alkynyl alkoxy alkane additives at concentrations ranging from ~0.05 to ~0.5 g/L. The surface finishes of the coated articles varied as a function of the additive concentration and the current density, and each coated article in this example produced using electrodeposition baths containing an additive demonstrated improved brightening/leveling in the deposited coating as compared to the reference sample (Article 1A). Here bright coatings were produced across a 200 ASF current density range. Increases in concentration produced brighter coatings at higher current densities than lower concentrations.

Example 2

This example demonstrates the use of hydroxy alkynes as brightening agents in the deposition of Ni—W alloy coatings. Articles in this example were produced in the same fashion as those in Example 1 described above.

Article 1A from Example 1 served as a reference for this example. As described above, the resulting Ni—W alloy coating produced from this solution was matte/semi-bright at a current density below 20 ASF and hazy/matte at a current density greater than 20 ASF.

Solution A from Example 1 was used as the basic electrolyte solution for the electrodeposition baths demonstrated in this example, and brightening agents were added to this solution in concentrations from ~0.02 to ~0.1 g/L.

Articles 2B-D were produced from electrodeposition baths containing Solution A and a hydroxy alkyne additive at concentrations ranging from ~0.02 g/L to ~0.1 g/L. The surface finish of the coated articles varied as a function of the additive concentration and the current density, and each coated article in Example 2 produced using electrodeposition baths containing an additive demonstrated improved brightening/leveling in the deposited coating as compared to the reference sample (Article 1A). Increases in concentration increased the brightness of the coatings at low to medium current densities.

Example 3

This example demonstrates the use of betains as brightening agents in the deposition of Ni—W alloy coatings. Articles in this example were produced in the same fashion as those in Example 1 described above.

Article 1A from Example 1 served as a reference for this example. As described above, the resulting Ni—W alloy coating produced from this solution was matte/semi-bright at a current density below 20 ASF and hazy/matte at a current density greater than 20 ASF.

Solution A from Example 1 was used as the basic electrolyte solution for the electrodeposition baths demonstrated in this example, and brightening agents were added to this solution in concentrations from ~0.1 to ~10 g/L.

Articles 3B-E were produced from electrodeposition baths containing Solution A and a betain additive at concentrations ranging from ~0.1 g/L to ~10 g/L. The surface finish of the coated articles varied as a function of the additive concentration and the current density, and each coated article in Example 3 produced using electrodeposition baths containing an additive demonstrated improved brightening/leveling in the deposited coating as compared to the reference sample (Article 1A). Increases in concentration increased the brightness of the coatings at low to medium current densities.

Example 4

This example demonstrates the use of polyalkoxylated naphthols as wetting agents in the deposition of Ni—W alloy coatings. Articles in this example were produced in the same fashion as those in Example 1 described above.

Article 1A from Example 1 served as a reference for this example. As described above, the resulting Ni—W alloy coating produced from this solution was matte/semi-bright at a current density below 20 ASF and hazy/matte at a current density greater than 20 ASF.

Solution A from Example 1 was used as the basic electrolyte solution for the electrodeposition baths demonstrated in this example, and wetting agents were added to this solution in concentrations from 0.1-1 g/L.

Articles 4B-F were produced from electrodeposition baths containing Solution A and wetting agents chosen from the polyalkoxylated naphthol and anionic fluorocarbon families at concentrations of 0.1-1.0 g/L. A small degree of brightening was observed at all concentrations of wetting agents relative to the reference (Article 1A). Coating conditions shown to produce pitting in the deposit with Solution A were evaluated using the wetting agents in conjunction with Solution A. Incorporation of the wetting agents demonstrated reduced, and in some cases completely eliminated, pitting defects from the coatings.

Example 5

This example demonstrates the combined use of two brightening agents in the deposition of Ni—W alloy coatings. Articles in this example were produced in the same fashion as those in Example 1 described above.

Article 1A from Example 1 served as a reference for this example. As described above, the resulting Ni—W alloy coating produced from this solution was matte/semi-bright at a current density below 20 ASF and hazy/matte at a current density greater than 20 ASF.

Solution A from Example 1 was used as the basic electrolyte solution for the electrodeposition baths demonstrated in this example, and combinations of the brightening agents used in Examples 1 (0.12, 0.5 g/L), 2 (0.05 g/L), and 3 (2 g/L) were added.

Articles 5B-E were produced from electrodeposition baths containing Solution A and combinations of the alkynyl alkoxy alkane, hydroxy alkyne, and betain additives. Complementary brightening/leveling was observed on coated articles in all examples, and each article in Example 5 produced using electrodeposition baths containing a combination of additives demonstrated improved brightening/leveling in the deposited coating as compared to the reference sample (Article 1A) and coated articles produced using electrodeposition baths containing only one brightening agent, as described in Examples 1, 2, and 3.

Example 6

This example demonstrates the combined use of a brightening agent and a wetting agent in the deposition of Ni—W alloy coatings. Articles in this example were produced in the same fashion as those in Example 1 described above.

Article 1A from Example 1 served as a reference for this example. As described above, the resulting Ni—W alloy coating produced from this solution was matte/semi-bright at a current density below 20 ASF and hazy/matte at a current density greater than 20 ASF.

Solution A from Example 1 was used as the basic electrolyte solution for the electrodeposition baths demonstrated in this example, and brightening (Example 1: 0.12 g/L, 0.24 g/L) and wetting (Example 4: 0.4 g/L) agents were added.

Articles 6B-C were produced from electrodeposition baths containing Solution A and the combination of a alkynyl alkoxy alkane and polyalkoxylated naphthol additives. Complementary coating quality, as evidenced by reduced propensity to surface pitting, was observed on coated articles produced from both electrodeposition baths as compared to coated articles produced using electrodeposition baths containing only one brightening agent, as shown in Examples 1 and 4. Each article in Example 6 demonstrated improved brightening/leveling in the deposited coating as compared to the reference sample (Article 1A).

Example 7

This example demonstrates the combined use of two brightening agents and a wetting agent in Ni—W alloy coatings. Articles in this example were produced in the same fashion as those in Example 1 described above.

Article 1A from Example 1 served as a reference for this example. As described above, the resulting Ni—W alloy coating produced from this solution was matte/semi-bright at a current density below 20 ASF and hazy/matte at a current density greater than 20 ASF.

Solution A from Example 1 was used as the basic electrolyte solution for the electrodeposition baths demonstrated in this example, and brightening agents (Example 1: 0.12 g/L, 0.24 g/L, 0.48 g/L; Example 2: 0.075 g/L) and a wetting agent (Example 4: 0.4 g/L) were added.

Articles 7B-D were produced from electrodeposition baths containing Solution A and combinations of a alkynyl alkoxy alkane, a hydroxy alkyne, and a polyalkoxylated naphthol. Complementary brightening/leveling and reduced propensity to surface pitting were observed on coated articles produced using each electrodeposition bath as compared to coated articles produced using electrodeposition baths containing only one brightening or wetting agent, as described in Examples 1, 2, 4, and as compared to coated articles produced using electrodeposition baths containing two additives, as described in Examples 5 and 6. Each article in Example 7 demonstrated improved brightening/leveling in the deposited coating as compared the reference sample (Article 1A).

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. An electrodeposition method comprising:
obtaining a sample from an electrodeposition bath comprising a tungsten and/or molybdenum ionic species, an ionic species of nickel, and a brightening agent comprising an alkynyl alkoxy alkane compound having the formula H—C≡C—$[CH_2]_n$—O—$[R^1]$, wherein n is an integer between 1 and 100, and $R^1$ is alkyl, optionally substituted;
analyzing the sample; and
electrodepositing a coating on an article in the electroplating bath, wherein the coating comprises tungsten and/or molybdenum, and nickel, wherein the coating has a nanocrystalline grain structure.

2. The method of claim 1, wherein the brightening agent comprises POPDH.

3. The method of claim 1, wherein the coating is electrodeposited using DC plating.

4. The method of claim 1, wherein the coating is electrodeposited using reverse pulse plating.

5. The method of claim 1, wherein analyzing the sample comprises determining the concentration of the brightening agent.

6. The method of claim 5, comprising adding a metal compound to the sample to react with the brightening agent to form a metal-bound species.

7. The method of claim 6, wherein the metal-bound species is analyzed to determine the concentration of the brightening agent.

8. The method of claim 1, wherein the bath comprises a wetting agent.

9. The method of claim 8, wherein the analyzing the sample comprises determining the concentration of the wetting agent.

10. The method of claim 9, wherein the wetting agent is sulfopropylated polyalkoxy napthol compound.

11. The method of claim 1, wherein the coating comprises a tungsten alloy.

12. The method of claim 11, wherein the coating comprises a nickel-tungsten alloy.

13. An electrodeposition method comprising:
obtaining a sample from an electrodeposition bath comprising a tungsten and/or molybdenum ionic species, an ionic species of nickel, and a brightening agent comprising POPS;

analyzing the sample; and electrodepositing a coating on an article in the electroplating bath, wherein the coating comprises tungsten and/or molybdenum, and nickel, wherein the coating has a nanocrystalline grain structure.

14. The method of claim 13, wherein the coating comprises a nickel-tungsten alloy.

* * * * *